United States Patent [19]

Odernheimer

[11] Patent Number: 4,541,268

[45] Date of Patent: Sep. 17, 1985

[54] METHOD AND DEVICE FOR THE SAMPLING OF TRACE ELEMENTS IN GASES, LIQUIDS, SOLIDS OR IN SURFACE LAYERS

[75] Inventor: Bernhard Odernheimer, Munster, Fed. Rep. of Germany

[73] Assignee: Bruker-Franzen Analytik GmbH, Bremen, Fed. Rep. of Germany

[21] Appl. No.: 504,688

[22] PCT Filed: Sep. 22, 1982

[86] PCT No.: PCT/DE82/00189

§ 371 Date: May 20, 1983

§ 102(e) Date: May 20, 1983

[87] PCT Pub. No.: WO83/01110

PCT Pub. Date: Mar. 31, 1983

[30] Foreign Application Priority Data

Sep. 23, 1981 [DE] Fed. Rep. of Germany ....... 3137765

[51] Int. Cl.⁴ .................................. G01N 13/00
[52] U.S. Cl. ........................................ 73/23; 73/19; 55/158
[58] Field of Search ............... 73/19, 23, 61 R; 55/158

[56] References Cited

U.S. PATENT DOCUMENTS

| 3,638,401 | 2/1972 | Kabler .................................. 55/158 |
| 3,681,032 | 8/1972 | Long ...................................... 73/19 |
| 3,797,318 | 3/1974 | Palm ................................ 73/863.21 |
| 3,929,003 | 12/1975 | Llewellyn ............................ 73/19 |
| 3,942,357 | 3/1976 | Jenkins ................................. 73/23 |
| 3,950,980 | 4/1976 | Braun et al. ........................ 73/23 |
| 3,985,017 | 10/1976 | Goldsmith ......................... 73/23 |
| 4,433,982 | 2/1984 | Odernheimer et al. ............. 73/19 |

FOREIGN PATENT DOCUMENTS

| 2022958 | 12/1970 | Fed. Rep. of Germany . |
| 2139992 | 2/1973 | Fed. Rep. of Germany . |
| 1573147 | 7/1969 | France . |
| WO81/02632 | 9/1981 | International . |

Primary Examiner—Stephen A. Kreitman
Attorney, Agent, or Firm—Parmelee, Bollinger & Bramblett

[57] ABSTRACT

The subject invention provides a method and apparatus for the sampling of trace elements in gas, liquids, solids or on surface layers. A collector surface having predetermined absorption characteristics is brought into contact with a material to be sampled. Thereafter, the collector surface is brought into contact with a contact membrane. The contact membrane is heated and swept by a carrier gas from the input head of an analysis apparatus to analyze the sample collected by the collector membrane. Trace elements in the sampling thermally desorbed by the collector surface are put in solution, are subject to diffusion and evaporation by traversing the contact member, and are transported by the carrier gas through a conduit to a gas analyzer for analysis. The use of both a collector surface cooperating with a contact member advantageously regenerates the collector surface so that it may be used in repeated sampling operations. The contact membrane is formed in a substantially regular geometric shape, preferably circular, so that it may be swept by the carrier case from its outer periphery to its center. The method and apparatus of the present invention provide enhancement sensitivity and speed in the analysis of trace elements to be detected.

13 Claims, 14 Drawing Figures

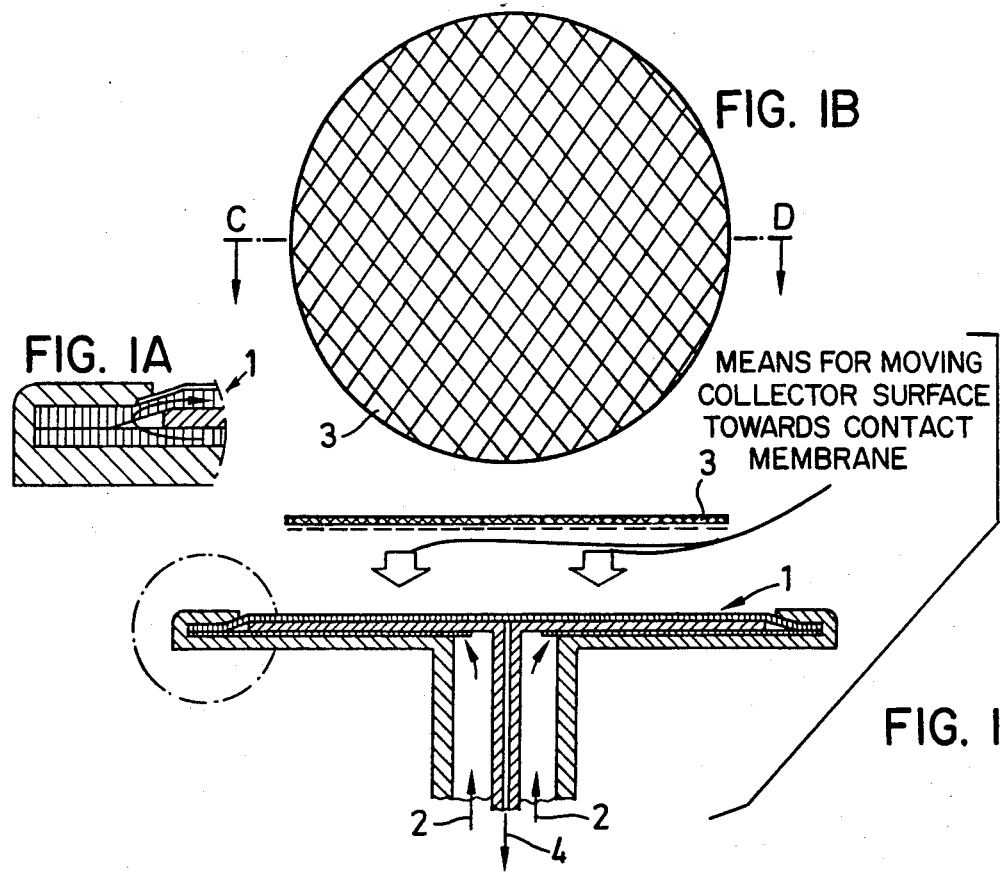
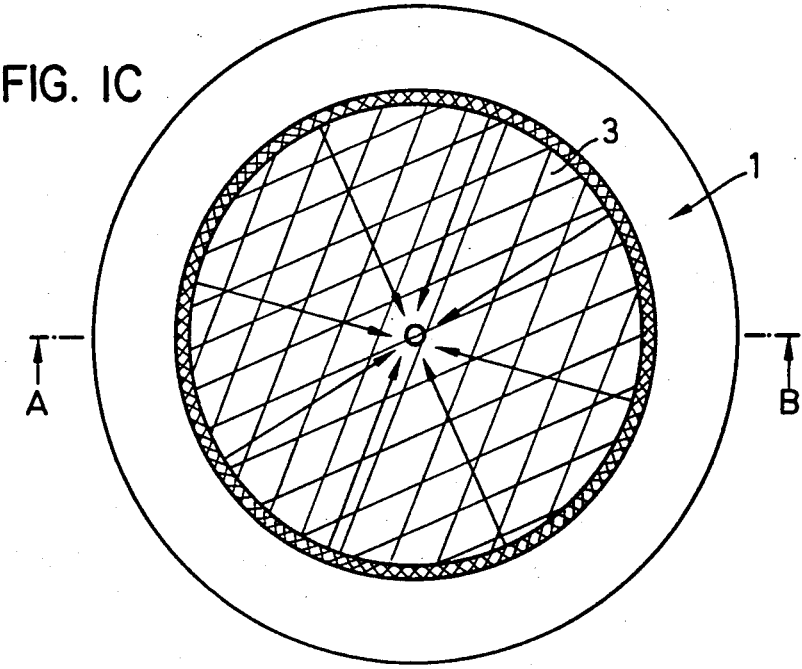

METHOD AND DEVICE FOR THE SAMPLING OF TRACE ELEMENTS IN GASES, LIQUIDS, SOLIDS OR IN SURFACE LAYERS

TECHNICAL FIELD

The invention relates to a method and apparatus for the sampling of trace elements in gases, liquids, on solids or in surface layers for the purpose of subsequent detection, identification or quantification.

STATE OF THE ART

It is known to detect the smallest traces of organic substances in gases, for example air, in liquids, for example water, as well as in and on solids by enriching the trace components by solvent extraction, adsorption by means of a gradient and sorption tube (filled, for example, with Tenax-GC, XAD-2, active carbon etc. as sorbents), or by freezing out. With heterogeneous systems, for example suspended matter in air or water, it is possible to use filters for the sampling, which on loading are subjected to a solvent extraction.

Traces enriched on gradient or sorption tubes from a gas by means of adsorption may be desorbed, if need be, with the help of a relatively simple pneumatic system by directly heating the traces in a carrier gas, and then admitted into the gas detector.

However, a labor-intensive and complicated preparation of the samples often connected with a loss of sample material due to volatilization or decomposition is required in most cases before the samples are loaded in the analyzer. This preparatory work requires a high degree of careful work and experience. If the analysis apparatus is a gas-chromatograph or a combination of GC/MS, the sample must be applied to the inlet of the separating column, for example with the help of an injection needle and through a septum in order to evaporate the solvent and trace components contained in said solvent.

The disadvantages of the procedures specified above are also known in particular with routine analyses with high amounts of sample throughput. Therefore, efforts have been made to load the analysis apparatus discontinuously or continuously with selectively enriched, volatile trace components in gases, liquids, aqueous slurries or solid granulates with the help of diaphragms and membrane separators. In such a procedure, a relative enrichment is achieved by way of the diaphragm-/membrane without increasing the partial pressure of the component to be measured after it has passed through the diaphragm/membrane. In the most favorable case, its partial pressure is equal the partial pressure before the membrane/diaphragm. Said techniques aim for the discontinuous detection of highly volatile substances such as lower alcohols, or of permanent gases such as oxygen and carbon monoxide, which are present in each case in relatively high concentrations (FR, A, No. 1573147/1969), or they require an extremely sensitive detector if carried out continuously, for example a mass spectrometer with a multi-stage, differentially evacuated membrane separator system (DE, A, No. 1673239/1970; DE, A, No. 2022958/1970; and DE, A, No. 2310264/1973). More recent applications specify an inlet head that can be used advantageously in a discontinuous operation as a GC inlet system, making the injection through a septum superfluous (DE, P, No. 3009069.8/1980, and PCT/DE No. 81/00043/1981). In this case, the sample is loaded, for example, by successively applying the solution to be tested to a contact membrane, which is flushed with carrier gas and adjusted to a relatively low temperature $T_1$, whereby the solvent evaporates and the trace components of the solution to be analylized, which components are concentrated in the contact membrane almost without any losses, pass into the carrier gas only after the temperature has been increased to $T_2$. If the temperatures $T_1$ and $T_2$ are adjusted or adapted to the gas-chromatographic mobility behavior of the trace component and the carrier gas throughflow volume and the dead volume between the membrane and detector is low, high partial pressures can be produced for short periods behind the contact membrane particularly by rapidly heating to the desorption temperature $T_2$ even with very low absolute amounts sorbated in the small volume of the membrane. Said partial pressures exceed the partial pressures of the trace components before the membrane by orders of magnitude and improve the signal/noise ratio of the detector to the same degree. The known inlet head permits also the highly sensitive and quantitative detection of poorly volatile substances present on a surface or in an adsorbing surface layer by contacting the sufficiently heated, strong contact membrane—which, however, should be as thin as possible—directly with the surface or surface layer to be tested.

THE INVENTION

The problem of the present invention is to enhance the sensitivity of the known receiver head and to develop an even more rapid analysis procedure for even more careful treatment of the materials tested.

Said problem is solved by the features contained in the characterizing clauses of the apparatus and process claims.

The contact membrane is designed in a way such that its geometric shape is as regular as possible, for example rectangular, square, pentagonal, hexagonal, octagonal and polygonal, or circular. Preferably, the contact membrane has a circular form. The carrier gas is conducted in a way such that it sweeps the contact membrane from the lateral edges toward the center. This ia achieved by conducting the carrier gas first against the outer edges of the contact membrane, using a feed pipe preferably centrally arranged on the bottom side of a supporting plate for the contact membrane, and from there towards the center of the contact membrane. This requires providing a discharge duct for the carrier gas in the geometric center of the contact membrane. Based on simple geometric considerations, the preferably trouble-free operation of such a system is assured if the contact membrane is provided with a circular form. In this case, the carrier gas flows from the circumference of the contact membrane to the center of the circular membrane, where the discharge duct for the carrier gas is extended directly up to the contact membrane.

A collecting surface suitable for enriching trace components from gas, liquids and solids is applied to the contact membrane. The quality of said collector surface must be such that the components to be analyzed are absorbed by said collector surface as selectively as possible. For many organic substances to be analyzed, it was found that an inert fabric covered with silicone rubber is useful as the adsorbing phase of the collector surface. However, the collecting surface may also consist of glass fibers, filter paper or glass-fiber filter paper, sheet metal coated with an adsorbing material, or glass plates covered with adsorbing material. Usefully, the surface is adapted to the shape of the surface of the contact membrane, which assures that the common contact area is as large as possible.

The process and apparatus are applied in a way such that the collecting surface is exposed to the medium to be tested, for example to air, water, sample of urine, blood, saliva or sweat, to the skin of a test person or patient, to a homogenized food sample, to a solvent extract, paint coating or another type of solid surface. Small proportions of the trace component to be analyzed will dissolve in each case in the collecting surface or its coating, which proportions are proportional to the concentration present in the sample medium. The collecting surface may be provided in the form of a filter disk on which suspended matter and other particles will be separated as air or liquids are sucked through said filter. If the filter disk subjected to such flow is covered with an adsorbing phase, also gaseous trace components can be enriched.

For the analysis of the adsorbed or mechanically separated substance traces, the collecting surface is taken to the contact membrane and heated. This will regenerate the collector surface if it is used in many applications, which means that it can be used several times. It is often useful to rinse the collecting surface with distilled water after the desorption of trace components has been sampled, and to then dry it mechanically by means of swabs.

The process and apparatus according to the invention can be refined further to a standardized, universal high-speed method for sampling and sample admittance for the detection, identification and quantitative determination of trace componets by means of GC, MS and a combination of GC/MS. The surface or surface layer, which is known to be capable of being tested with the contact membrane of the receiving head for the presence of any contaminants, is advantageously designed in a way such that it is suitable as a well-defined and standardized collector surface for enriching trace components from gases, liquids and solids.

For the quantitative evaluation of the traces detected with the collector surface as a representative sample, the collector surface itself, which may be standardized, for example with respect to material, surface, type of coating and thickness of the coating, sorption selectivity and capacity and thermal capacity, the temperatures of the collector surface and contact membrane, the duration of action and type of action, for example gas or liquid in a state of rest and in flow, solids powdered or with smooth surfaces, as well as the contact time for the desorption on the contact membrane must be defined in a manner familiar to the expert, namely in a way such that such definition will be adequate for the accuracty required in each case when the yield of measurement signals are correlated with the concentration or coating thickness actually present in or on the medium tested.

Also, the contact membrane itself may serve as the collector surface.

One or several collector surfaces may be component(s) of the receiver head and taken to the contact membrane in an alternating way, i.e., collector phase/-heating phase. Such an arrangement is particularly suitable as a probe for monitoring the air (FIG. 2).

Advantageous is the application of the receiver head as an evaluation system for thin-layer chromatography. In the simplest case, the stain or spot on the thin-layer plate is contacted with the contact membrane.

Moreover, the method according to the invention readily permits combining the liquid (LC) and high-pressure liquid chromatography (HPLC) with a mass spectrometer. The fractions eluating with the mobile phase may be concentrated individually on collector surfaces and admitted to the ion source of the mass spectrometer (MS) by way of the contact membrane.

For some applications, it is advantageous if the collector surface is capable of selective chemosorption or of derivatizing defined components by providing it with special coatings. Basic components such as, for example, alkaloids, are adsorbed selectively reversibly by an acid coating, and alcohols are dehydrated to products with superior GC-practicability when heating is carried out in the presence of dehydrating agents.

Derivatizing, for example the preparation of trimethylsilyl derivatives, can be carried out readily in the presence of a collector surface with nonpolarized coating or covering which, due to its low polarity, will preferably adsorb the derivative when the reaction mixture is cooled.

Finally, for the purpose of their identification on the basis of characteristic volatile components, bacteria or pyrolysis products can be transferred to a collecting surface by means of a simple dabbing technique and analyzed in accordance with the present invention.

For facilitating the quantitative evaluation, it is often useful to apply an internal standard.

Once optimal parameters have been found for a given field of application, such parameters can be kept constant without problems with the help of conventional laboratory aids such as thermostats and stop watches. For many applications, the sampling and evaluation cycle is readily accessible for automatic controls.

BRIEF DESCRIPTION OF THE DRAWINGS

FIG. 1 illustrates a sectional view of an apparatus in accordance with the present invention including a contact membrane and a collector surface movable into and out of contact with the contact membrane;

FIG. 1A illustrates a detailed portion of one end of the contact membrane and its supporting structure indicating fluid flow therebetween;

FIG. 1B illustrates a top plan view of the collector surface of FIG. 1;

FIG. 1C illustrates a top plan view of the contact membrane of FIG. 1 with the collector surface above it;

BRIEF DESCRIPTION OF THE FIGURES AND BEST EMBODIMENTS OF THE INVENTION

Figure 2:
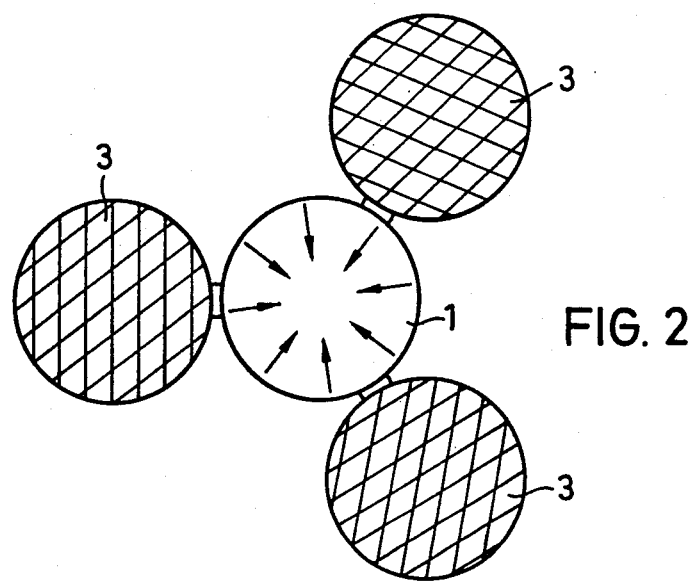
FIG. 2 schematically illustrates three equal collecting surfaces and a single contact membrane.

FIGS. 1–1C show in a sectional and top view the embodiment of a suitable apparatus comprising a contact membrane 1 flushed from behind by a carrier gas 2, and a collector surface 3 which, in the present embodiment, is a round piece of inert fabric covered by an adsorbing phase, for example silicone rubber. The collector surface may also be a thin glass fiber filter paper, a metal sheet covered with an adsorbing material, or a glass plate. A top plan view of the collector surface 3 is illustrated by FIG. 1B. Its surface may have any form, however, it is usefully adapted to the form of the surface of the contact membrane in order to assure the largest possible common contact area and efficient heat and material exchange, i.e., the dead volume between the collector surface and the detector 4 (not shown in the figure) should be small, so that high concentrations can be built up in the carrier gas.

FIG. 1 illustrates in section, the collector surface 3, as it is moved towards the contact membrane 1 in the direction of the two larger arrows of the drawing Figure. The contact membrane is flushed from behind with a carrier gas flowing in the direction illustrated by arrows 2 through suitably provided ducts. As illustrated in FIG. 1A, as the gas 2 approaches the periphery of the contact membrane, its direction of flow is reversed so that it sweeps the contact membrane in a direction towards the geometric center thereof, as illustrated by the arrows in FIG. 1C. The carrier gas is discharged through a discharge duct 5 in fluid communication with the geometrical center of the contact membrane as illustrated in FIGS. 1 and 1C.

FIG. 2 schematically illustrates a system incorporating three equal collector surfaces 3 attached to a single contact membrane 1. Each collector surface 3 may be alternatively and selectively brought into contact with the single contact membrane.

Figure 2A:
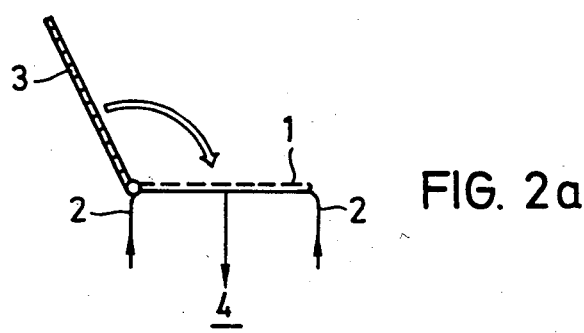
FIG. 2a illustrates a collecting surface as it approaches a contact membrane in the direction shown by the arrow.
Figure 2B:
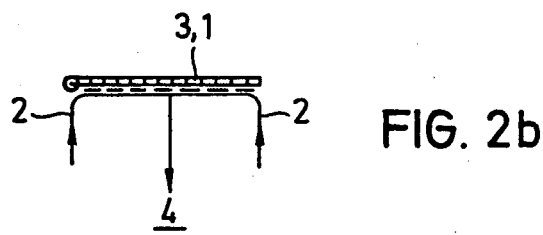
FIG. 2b illustrates the collecting surface of FIG. 2a when it is brought flush against the contact membrane.

FIG 2a illustrates schematically one collector surface 3 being moved in a direction towards the contact membrane 1. Arrows 2 illustrate the flow of a carrier gas across the surface of the contact membrane in a direction from its periphery towards its center, and the downwardly directed arrow illustrates the discharge of the carrier gas from the center of the contact membrane towards a detector 4. FIG. 2b is similar to FIG. 2a except that the collector surface 3 is shown flush up against the contact membrane 1.

Figure 3:
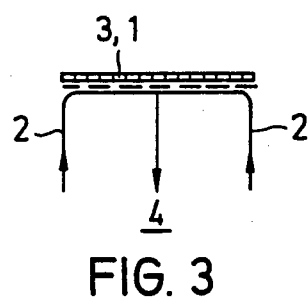
FIG. 3 illustrates a collecting surface flush against a contact member.
Figure 3A:
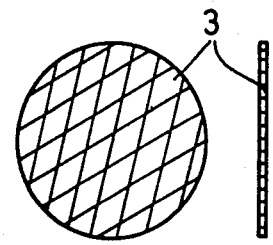
FIG. 3a illustrates the collecting surface of FIG. 3 in plan view and in section to illustrate that the collecting surface is circular and open pored.
Figure 3B:
FIG. 3b schematically illustrates a collecting surface flush against a solid surface.
Figure 3C:
FIG. 3c schematically illustrates a collector surface in the form of a filter disk for collecting particles as air and liquids flow through the filter.
Figure 3D:
FIG. 3d schematically illustrates the collection of gas flowing against the collecting surface.
Figure 3E:
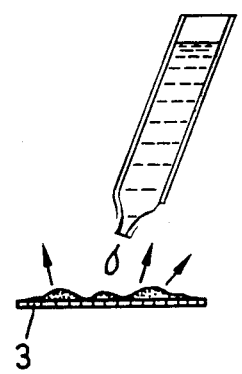
FIG. 3e schematically illustrates the application of a liquid solution to a solid sample on the collecting surface.
Figure 3F:
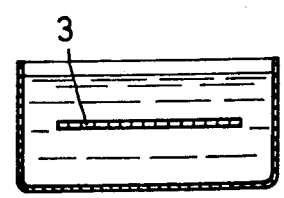
FIG. 3f schematically illustrates a collecting surface immersed in a liquid sample.

FIG. 3 is identical to FIG. 2b and shows a collector surface 3 flush against a contact membrane 1. FIG. 3a shows a circular open pored collector surface in a plan and sectional view. FIGS. 3a–3f illustrate schematically how different types of sample materials are applied to the collector surface 3. FIG. 3b schematically illustrates the collector surface 3 applied directly to a solid sample material. FIG. 3c schematically illustrates a collector surface 3 which is formed as a disk filter for collecting particles contained in air or liquid which flow through the collector surface. FIG. 3d illustrates air or gas flowing against the collector surface, while FIG. 3e illustrates a liquid solution applied to dissolve solid material on the collector surface. Finally, FIG. 3f illustrates the collector surface totally immersed in a liquid to be sampled.

The invention offers a simple, universally applicable and extremely rapid method of sampling and sample receiving for the qualitative and quantitative analysis of traces by means of gas-chromatography, mass spectrometry and combined GC/MS techniques. The method is particularly advantageous for numerous routine applications in environmental analytics, for the analysis of foodstuffs and residues, process and quality control, in medical-clinical analytics, toxicology, microbiology, experimental zoology, pharmacology, doping control, criminal investigations and court medicine.

Gas-chromatographs, mass spectrometers and combination GC/MS-equipment equipped with conventional injectors or receiving systems may be refitted with the apparatus of the present invention at low costs.

For the sampling, enrichment and, if need be, aimed chemical reaction, a usefully selectively adsorbing, standardized collector surface is subjected to the gas, liquid or solid material by contact under defined conditions and, for the analysis of the sorbate and/or its reaction products, subsequently taken to the heatable contact membrane of the receiving head of an analyzer, said membrane being flushed from behind with a carrier gas. In the course of dissolution, diffusion and evaporation, the trace components so desorbed quantitatively thermally by the collector surface pass through the contact membrane and into the carrier gas, and supplied by said gas to a gas analyzer, for example a mass spectrometer (MS) by way of a sample conduit or gas-chromatographic separating column.

I claim:

1. Method of sampling trace components in gases, liquids, solids or in surface layers for the purpose of detection, identification or quantification, the steps of said method including:

exposing a collector surface to a material to be sampled, applying said collector surface to a heatable contact membrane of a receiving head of an analysis apparatus, and flushing said contact membrane with a carrier gas along the surface thereof which is not in contact with said collector surface for transporting trace components to be analyzed.

2. The method as defined in claim 1, characterized by the fact that for the sampling or enrichment of trace components, the collector surface is exposed to the gas, liquid or solid material at a low temperature, and that on contact of the collector surface with the contact membrane at a higher temperature, the trace component is thermally desorbed into the carrier gas.

3. The method as defined in claim 1, characterized by the fact that the contact membrane itself functions as the collector surface.

4. The method as defined in claim 1, characterized by the fact that several collector surfaces are used, said surfaces being alternatingly contacted with the contact membrane.

5. The method as defined in claim 1, characterized by the fact that the rate of throughflow of carrier gas can be kept as low as possible by avoiding dead volumes between the collector surface and contact membrane as well as between the contact membrane and detector.

6. The method as defined in claim 1, characterized by the fact that the collector surfaces are components of a probe for monitoring the air, soil or open waters.

7. The apparatus for carrying out the method defined in claim 1, characterized by a collector surface (3) having inert fabric, glass fibers, filter paper or glass fiber filter paper, sheel metal or glass plates.

8. Apparatus as defined in claim 7, characterized by the fact that the materials are coated with a polymer substance.

9. Apparatus as defined in claim 8, characterized by the fact that the polymer substance is silicone rubber.

10. Apparatus for sampling trace components in gases, liquids, solids or in surface layers for the purpose of detection, identification or quantification, said apparatus including:
   a collector surface adapted to collect a sampling of material to be analyzed,
   a heatable contact membrane supported on a supporting plate,
   means for selectively moving said collector surface in and out of contact with a top surface of said contact membrane to transfer said sampling of material on said collector surface to said contact membrane,
   conduit means in fluid communication with the bottom surface of said contact membrane through said supporting plate for flushing said bottom surface with a carrier gas in a direction from the periphery of said contact membrane towards the center thereof, and
   a discharge conduit in fluid communication with the proximate geometrical center of the bottom surface of said contact membrane for discharging said carrier gas.

11. The apparatus as defined in claim 10, characterized by the fact that the contact membrane (1) is circular or provided in another geometrically regular form.

12. Apparatus as defined in claim 10, characterized by the fact that a collector surface (3) is applied to the contact membrane (1).

13. Apparatus as defined in claim 10, characterized by the fact that the shape of the surface of the collector (3) is adapted to the shape of the surface of the contact membrane (1).

* * * * *